United States Patent
Faraon et al.

(10) Patent No.: US 10,881,336 B2
(45) Date of Patent: Jan. 5, 2021

(54) PLANAR DIFFRACTIVE DEVICE WITH MATCHING DIFFRACTION SPECTRUM

(71) Applicant: CALIFORNIA INSTITUTE OF TECHNOLOGY, Pasadena, CA (US)

(72) Inventors: Andrei Faraon, La Canada Flintridge, CA (US); Amir Arbabi, Pasadena, CA (US); Yu Horie, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 15/241,914

(22) Filed: Aug. 19, 2016

(65) Prior Publication Data
US 2017/0188901 A1 Jul. 6, 2017

Related U.S. Application Data

(60) Provisional application No. 62/208,447, filed on Aug. 21, 2015.

(51) Int. Cl.
*A61B 5/1455* (2006.01)
*A61B 5/145* (2006.01)
(Continued)

(52) U.S. Cl.
CPC ........ *A61B 5/1455* (2013.01); *A61B 5/14532* (2013.01); *A61B 5/14546* (2013.01); *G01J 3/12* (2013.01); *G01J 3/18* (2013.01); *G01J 3/44* (2013.01); *G01N 21/65* (2013.01); *G02B 27/1006* (2013.01); *G02B 27/1086* (2013.01); *A61B 2560/0431* (2013.01); *A61B 2562/0238* (2013.01); *A61B 2562/0285* (2013.01);
(Continued)

(58) Field of Classification Search
CPC .............. A61B 5/1455; A61B 5/14532; A61B 5/14546; G01N 21/65
USPC ...................................................... 422/82.05
See application file for complete search history.

(56) References Cited

U.S. PATENT DOCUMENTS 8,830,556 B2  9/2014  Smith et al.
8,994,059 B2  3/2015  Huh et al.
(Continued)

FOREIGN PATENT DOCUMENTS

KR   1020140113553 A   9/2014
WO   2015/063762 A1    5/2015
(Continued)

OTHER PUBLICATIONS

Shao, J. et al. (2012). "In Vivo Blood Glucose Quantification Using Raman Spectroscopy." PLOS One. 7(10). e48127. (Year: 2012).*
(Continued)

*Primary Examiner* — Benjamin R Whatley
*Assistant Examiner* — Jacqueline Brazin
(74) *Attorney, Agent, or Firm* — Steinfl + Bruno LLP

(57) ABSTRACT

A solution containing a target molecule and a reference molecule is illuminated to obtain Raman signals. An optical metasurface is used as a diffractive optical element to split the Raman signal from the target molecule and the Raman signal from the reference molecule. The target and reference Raman signals can be detected at different locations with different photodetectors, and the target molecule concentration in the solution is determined by comparing the target and reference Raman signals.

4 Claims, 2 Drawing Sheets

(51) Int. Cl.
    *G01N 21/65* (2006.01)
    *G01J 3/44* (2006.01)
    *G02B 27/10* (2006.01)
    *G01J 3/18* (2006.01)
    *G01J 3/12* (2006.01)

(52) U.S. Cl.
    CPC ........... *G01J 2003/1213* (2013.01); *G01N 2201/068* (2013.01)

(56) References Cited

U.S. PATENT DOCUMENTS

| | | |
|---|---|---|
| 9,054,424 B1 | 6/2015 | Hunt et al. |
| 9,385,435 B2 | 7/2016 | Bily et al. |
| 9,448,305 B2 | 9/2016 | Bowers et al. |
| 9,450,310 B2 | 9/2016 | Bily et al. |
| 9,482,796 B2 | 11/2016 | Arbabi et al. |
| 9,507,064 B2 | 11/2016 | Brongersma et al. |
| 9,618,680 B2 | 4/2017 | Baker et al. |
| 9,658,469 B2 | 5/2017 | Pugh et al. |
| 9,711,852 B2 | 7/2017 | Chen et al. |
| 9,733,545 B2 | 8/2017 | Belkin et al. |
| 9,806,414 B2 | 10/2017 | Chen et al. |
| 9,806,415 B2 | 10/2017 | Chen et al. |
| 9,806,416 B2 | 10/2017 | Chen et al. |
| 9,812,779 B2 | 11/2017 | Chen et al. |
| 9,995,859 B2 | 6/2018 | Kamali et al. |
| 9,995,930 B2 | 6/2018 | Arbabi et al. |
| 10,199,415 B2 | 2/2019 | Akselrod et al. |
| 10,267,956 B2 | 4/2019 | Arbabi et al. |
| 10,267,957 B2 | 4/2019 | Kamali et al. |
| 10,488,651 B2 | 11/2019 | Kamali et al. |
| 2003/0169504 A1 | 9/2003 | Kaminsky et al. |
| 2003/0170442 A1 | 9/2003 | Kaminsky et al. |
| 2003/0175004 A1 | 9/2003 | Garito et al. |
| 2003/0176777 A1* | 9/2003 | Muller-Dethlefs ............ A61B 5/14532 600/322 |
| 2005/0062928 A1 | 3/2005 | Yau et al. |
| 2005/0203364 A1 | 9/2005 | Monfre et al. |
| 2006/0176471 A1* | 8/2006 | Hendriks ............ G01J 3/02 356/39 |
| 2006/0250613 A1* | 11/2006 | Demuth ............ G01J 3/32 356/301 |
| 2006/0276713 A1* | 12/2006 | Maier ............ A61B 5/14532 600/473 |
| 2007/0019306 A1 | 1/2007 | Wu et al. |
| 2007/0060806 A1 | 3/2007 | Hunter et al. |
| 2008/0161194 A1 | 7/2008 | Turner et al. |
| 2008/0186483 A1* | 8/2008 | Kiesel ............ A61B 5/14532 356/246 |
| 2008/0219027 A1 | 9/2008 | Bourdelais et al. |
| 2009/0250110 A1 | 10/2009 | Yu et al. |
| 2010/0252721 A1* | 10/2010 | Xu ............ G01J 3/0216 250/226 |
| 2011/0105867 A1 | 5/2011 | Schultz et al. |
| 2011/0141541 A1 | 6/2011 | Bratkovski |
| 2011/0210459 A1 | 9/2011 | Bille |
| 2012/0038915 A1 | 2/2012 | Tsuchida et al. |
| 2012/0082863 A1 | 4/2012 | Ohta et al. |
| 2012/0113419 A1* | 5/2012 | Wang ............ B82Y 15/00 356/301 |
| 2013/0208332 A1 | 8/2013 | Yu et al. |
| 2013/0337436 A1* | 12/2013 | Toury ............ B82Y 15/00 435/5 |
| 2014/0085693 A1 | 3/2014 | Mosallaei et al. |
| 2014/0124033 A1 | 5/2014 | Dimitrakopoulos et al. |
| 2014/0146390 A1 | 5/2014 | Kaempfe et al. |
| 2014/0167022 A1 | 6/2014 | Huh et al. |
| 2014/0264998 A1 | 9/2014 | Smith et al. |
| 2014/0277433 A1 | 9/2014 | Pugh et al. |
| 2014/0277436 A1 | 9/2014 | Pugh et al. |
| 2015/0117032 A1 | 4/2015 | Hu et al. |
| 2015/0124480 A1 | 5/2015 | Baker et al. |
| 2015/0219806 A1 | 8/2015 | Arbabi et al. |
| 2015/0255876 A1 | 9/2015 | Volpe |
| 2015/0309218 A1 | 10/2015 | Shalaev et al. |
| 2015/0323385 A1* | 11/2015 | Han ............ G01J 3/36 356/300 |
| 2016/0025914 A1 | 1/2016 | Brongersma et al. |
| 2016/0041095 A1* | 2/2016 | Rothberg ............ G01N 21/6408 506/4 |
| 2016/0299337 A1 | 10/2016 | Arbabi et al. |
| 2016/0306079 A1 | 10/2016 | Arbabi et al. |
| 2016/0313477 A1 | 10/2016 | Orenstein et al. |
| 2016/0320531 A1 | 11/2016 | Kamali et al. |
| 2017/0010483 A1 | 1/2017 | Fainman et al. |
| 2017/0030773 A1 | 2/2017 | Han et al. |
| 2017/0045652 A1 | 2/2017 | Arbabi et al. |
| 2017/0097558 A1 | 4/2017 | Belkin et al. |
| 2017/0195652 A1 | 7/2017 | Du et al. |
| 2017/0195659 A1 | 7/2017 | Du et al. |
| 2017/0212285 A1 | 7/2017 | Arbabi et al. |
| 2017/0250577 A1 | 8/2017 | Ho et al. |
| 2017/0351111 A1 | 12/2017 | Jeong et al. |
| 2018/0006376 A1 | 1/2018 | Black et al. |
| 2018/0042527 A1* | 2/2018 | Rawicz ............ A61B 3/0008 |
| 2018/0275321 A1 | 9/2018 | Kamali et al. |
| 2018/0292644 A1 | 10/2018 | Kamali et al. |

FOREIGN PATENT DOCUMENTS

| | | |
|---|---|---|
| WO | 2016/140720 A2 | 9/2016 |
| WO | 2017/034995 A1 | 3/2017 |
| WO | 2017/176343 A2 | 10/2017 |
| WO | 2017/176921 A1 | 10/2017 |

OTHER PUBLICATIONS

Aieta, F. et al., "Aberrations of Flat Lenses and Aplanatic Metasurfaces.", Optics Express, vol. 21, No. 25, pp. 31530-31539, (2013).
Aieta, F. et al., "Aberrations-Free Ultrathin Flat Lenses and Axicons at Telecom Wavelengths Based on Plasmonic Metasurfaces.", Nano Lett., 12, pp. 4932-4936, (2012).
Aieta, F. et al., "Multiwavelength Achromatic Metasurfaces by Dispersive Phase Compensation.", Science, vol. 347, Issue 6228, pp. 1342-1345, (2015), 5 pages.
Arbabi, A. et al., "Complete Control of Polarization and Phase of Light with High Efficiency and Sub-Wavelength Spatial Resolution.", arXiv:1411.1494 Physics Optics, 10 pages, (2014).
Arbabi, A. et al., "Controlling the Phase Front of Optical Fiber Beams using High Contrast Metastructures.", CLEO, 2 pages, (2014).
Arbabi, A. et al., "Efficient High NA Flat Micro-Lenses Realized Using High Contrast Transmitarrays.", Proc. SPIE, 7 pages, (2015).
Arbabi, A. et al., "Fundamental Limits of Ultrathin Metasurfaces.", arXiv:1411.2537, 6 pages, (2014).
Arbabi, A. et al., "Highly Efficient Polarization Control Using Subwavelength High Contrast Transmitarrays.", Proc. SPIE 9372, High Contrast Metasurfaces IV, (2015), 7 pages.
Arbabi, A. et al., "Subwavelength-Thick Lenses with High Numerical Apertures and Large Efficiency Based on High-Contrast Transmitarrays.", Nature Commun., 6:7069, 6 pages, (2015).
Arbabi, A. et al., "Subwavelength-Thick Lenses with High Numerical Apertures and Large Efficiency Based on High-Contrast Transmitarrays.", arXiv:1410.8261 Physics Optics, 10 pages, (2014).
Astilean, S. et al., "High-Efficiency Subwavelength Diffractive Element Patterned in a High-Refractive-Index Material for 633 nm.", Optics Letters, vol. 23, No. 7, pp. 552-554, 4 pages, (1998).
Bennett, S.J., "Achromatic Combinations of Hologram Optical Elements.", Applied Optics, vol. 15, No. 2, pp. 542-545, (1976).
Buralli, D.A. et al., "Some Fundamental Limitations of Achromatic Holographic Systems.", J. Opt. Soc. Am. A., vol. 6, No. 12, pp. 1863-1868, (1989).
Cheng, J. et al., "Truly Achromatic Optical Metasurfaces: A Filter Circuit Theory-Based Design.", J. Opt. Soc. Am. B, vol. 32, No. 10, pp. 2115-2121, (2015).

(56) References Cited

OTHER PUBLICATIONS

Di Falco, A. et al., "Flexible metamaterials at visible wavelengths.", New J. Phys. 12, 113006, 8 pages, (2010).
Eisenbach, O. et al., "Metasurfaces Based Dual Wavelength Diffractive Lenses.", Optics Express, vol. 23, No. 4, pp. 3928-3936, (2015).
Ergin, T. et al., "Three-Dimensional Invisibility Cloak at Optical Wavelengths.", Science, vol. 328, pp. 337-339, 4 pages, (2010).
Fan, P. et al., "An Invisible Metal-Semiconductor Photodetector.", Nature Photonics, vol. 6, pp. 380-385, (2012).
Fattal, D. et al., "Flat Dielectric Grating Reflectors with Focusing Abilities.", Nat. Photon. 4, pp. 466-470, (2010).
He, J. et al., "Inorganic Materials and Assembly Techniques for Flexible and Stretchable Electronics.", Proc. IEEE, vol. 103, No. 4, pp. 619-632, (2015).
HOLO/OR, The Early Pioneer of Diffractive Optics Since 1989, Taihei Boeki Co., Ltd., Retrieve:http://www.taiheiboeki.co.jp/product/201111HoloOr-DOE.pdf., Nov. 2011, 30 pages. (Chinese Original + English Translation).
Karimi, E. et al., "Generating Optical Orbital Angular Momentum at Visible Wavelengths Using a Plasmonic Metasurface.", Light Sci. Appl. 3, e167, 4 pages, (2014).
Khorasaninejad, M. et al., "Achromatic Metasurface Lens at Telecommunication Wavelengths.", Nano Lett., 15, pp. 5358-5362, 5 pages, (2015).
Kildishev, A. V. et al., "Planar Photonics with Metasurfaces.", Science 339, 1232009, 9 pages, (2013).
Knapp, D.J., "Fundamentals of Conformal Dome Design.", International Optical Design Conference, Proceedings of SPIE, vol. 4832, pp. 394-409, (2002), 17 pages.
Lalanne, P. et al., "Design and Fabrication of Blazed Binary Diffractive Elements with Sampling Periods Smaller than the Structural Cutoff.", J. Opt. Soc. Am. A, vol. 16, No. 5, pp. 1143-1156, (1999).
Latta, J.H., "Analysis of Multiple Hologram Optical Elements with Low Dispersion and Low Aberrations.", Applied Optics, vol. 11, No. 8, pp. 1686-1696, (1972).
Lin, D. et al., Dielectric Gradient Metasurface Optical Elements. Science, vol. 345, Issue 6194, 298-302, 6 pages, (2014).
Liu, V. et al., "S4: A Free Electromagnetic Solver for Layered Periodic Structures.", Comput. Phys. Commun. 183, pp. 2233-2244, (2012).
Ni, X. et al., "An Ultrathin Invisibility Skin Cloak for Visible Light.", Science, vol. 349, Issue 6254, pp. 1310-1314, 6 pages, (2015).
Oskooi, A. et al., "MEEP: A Flexible Free-Software Package for Electromagnetic Simulations by the FDTD Method.", Comput. Phys. Commun., vol. 181, pp. 687-702, 30 pages, (2010).
Piggott, A.Y. et al., "Inverse Design and Demonstration of a Compact and Broadband On-Chip Wavelength Demultiplexer.", Nature Photonics, vol. 9, pp. 374-377, (2015), 5 pages.
Pryce, I. et al., "Highly Strained Compliant Optical Metamaterials with Large Frequency Tunability.", Nano Lett. 10, pp. 4222-4227, (2010).
Shannon, R.R., "Overview of Conformal Optics.", PROC. SPIE 3705, Window and Dome Technologies and Materials VI, pp. 180-188, (1999), 11 pages.
Swanson, G.J. "Binary Optics Technology: The Theory and Design of Multi-Level Diffractive Optical Elements.", Technical Report 854, DTIC Document, 53 pages, (1989).
Sweatt, W.C., "Achromatic Triplet Using Holographic Optical Elements.", Applied Optics, vol. 16, No. 5, pp. 1390-1391, (1977).
Teo, J. et al., "Controlling Electromagnetic Fields at Boundaries of Arbitrary Geometries.", arXiv preprint arXiv:1509.06175, 11 pages, (2015).
Thompson, K. P. et al., "Freeform Optical Surfaces: A Revolution in Imaging Optical Design.", Opt. Photon. News 23, pp. 30-35, (2012).
Valentine, J. et al., "An Optical Cloak made of Dielectrics.", Nat. Mater., vol. 8, pp. 568-571, (2009).
Viventi, J. et al., "Flexible, Foldable, Actively Multiplexed, High-Density Electrode Array for Mapping Brain Activity In Vivo.", Nat. Neurosci. 14(12), pp. 1599-1605, 20 pages, (2011).
Vo, S. et al., "Sub-Wavelength Grating Lenses with a Twist.", IEEE Photon. Technol. Lett., vol. 26, No. 13, pp. 1375-1378, (2014).
Walia, S. et al., "Flexible Metasurfaces and Metamaterials: A Review of Materials and Fabrication Processes at Micro- and Nano-Scales.", Appl. Phys. Rev. 2, 011303, 16 pages, (2015).
Wang, Y. et al., "Achromatic Fresnel Optics for Wideband Extreme-Ultraviolet and X-Ray Imaging.", Nature, vol. 424, pp. 50-53, (2003).
Wang, C. et al., "User-Interactive Electronic Skin for Instantaneous Pressure Visualization.", + Supplementary Information, Nat. Mater., vol. 12, pp. 899-904, 23 pages, (2013).
Weingartner, I. et al., "Chromatic Correction of Two- and Three-Element Holographic Imaging Systems.", Optica Acta, vol. 29, No. 4, pp. 519-529, (1982), 15 pages.
Xu, X. et al., "Flexible Visible-Infrared Metamaterials and Their Applications in Highly Sensitive Chemical and Biological Sensing.", Nano Lett. 11, pp. 3232-3238, (2011).
Young, M., "Zone Plates and their Aberrations.", J. Opt. Soc. Am., vol. 62, No. 8, pp. 972-976, (1972).
Yu, N. et al., "Flat Optics with Designer Metasurfaces.", Nat. Mater., vol. 13, pp. 139-150, (2014).
Zheng, G. et al., "Metasurface Holograms Reaching 80% Efficiency.", Nature Nanotechnology, 10, pp. 1-5, (2015), 6 pages.
Zhao, Z. et al., "Multispectral Optical Metasurfaces Enabled by Achromatic Phase Transition.", Scientific Reports, 5:15781, 9 pages, (2015).
Zhu, L. et al., "Flexible Photonic Metastructures for Tunable Coloration.", Optica, vol. 2, No. 3, pp. 255-258, (2015).
Restriction Requirement for U.S. Appl. No. 15/097,101, filed Apr. 12, 2016 on behalf of California Institute of Technology. dated Aug. 17, 2017. 6 pages.
Notice of Allowance for U.S. Appl. No. 15/097,101, filed Apr. 12, 2016 on behalf of California Institute of Technology. dated Jan. 11, 2018. 11 pages.
International Search Report for PCT/US2016/047811 filed Aug. 19, 2016 on behalf of California Institute of Technology. dated Oct. 31, 2016. 8 pages.
Written Opinion for PCT/US2016/047811 filed Aug. 19, 2016 on behalf of California Institute of Technology. dated Oct. 31, 2016. 8 pages.
International Search Report for PCT/US2016/027086 filed Apr. 12, 2016 on behalf of California Institute of Technology. dated Jul. 20, 2016. 3 pages.
Written Opinion for PCT/US2016/027086 filed Apr. 12, 2016 on behalf of California Institute of Technology. dated Jul. 20, 2016. 3 pages.
International Search Report for PCT/US2016/027154 filed Apr. 12, 2016 on behalf of California Institute of Technology. dated Jul. 20, 2016. 4 pages.
Written Opinion for PCT/US2016/027154 filed Apr. 12, 2016 on behalf of California Institute of Technology. dated Jul. 20, 2016. 5 pages.
Arbabi, A. et al., "Dielectric Metasurfaces for Complete Control of Phase and Polarization with Subwavelength Spatial Resolution and High Transmission.", Nat. Nanotech., 28 pages, (2015).
Non-Final Office Action issued for U.S. Appl. No. 15/096,615, filed Apr. 12, 2016 on behalf of California Institute of Technology. dated Oct. 29, 2018. 16 pages.
Non-Final Office Action issued for U.S. Appl. No. 15/975,521, filed May 9, 2018 on behalf of California Institute of Technology. dated Sep. 18, 2018. 10 pages.
Notice of Allowance issued for U.S. Appl. No. 15/097,101, filed Apr. 12, 2016 on behalf of California Institute of Technology. dated Apr. 20, 2018. 12 pages.
Restriction Requirement issued for U.S. Appl. No. 15/096,615, filed Apr. 12, 2016 on behalf of California Institute of Technology. dated May 30, 2018. 7 pages.
Shao, J. et al., "In Vivo Blood Glucose Quantification Using Raman Spectroscopy.", PLOS One, vol. 7, Issue 10, e48127, 6 pages, (2012).

(56) References Cited

OTHER PUBLICATIONS

Staude et al., "Tailoring Directional Scattering through Magnetic and Electric Resonances in Subwavelength Silicon Nanodisks", ACS Nano, Aug. 2013, 7 (9), pp. 7824-7832.
West et al. "All-dielectric subwavelength metasurface focusing lens", Oct. 2014, vol. 22, No. 21, Optics Express 26212-26221.
Notice of Allowance for U.S. Appl. No. 15/975,521, filed May 9, 2018, on behalf of California Institute of Technology. dated Jan. 22, 2019. 10 pages.
Notice of Allowance for U.S. Appl. No. 15/096,615, filed Apr. 12, 2016, on behalf of California Institute of Technology. dated Feb. 13, 2019. 12 pages.
Arbabi E., "Multi-wavelength Optical Dieletric Metasurfaces" CIT 7159-P 1-6., 2015, 2 pages.
Arbabi, A., et al., "Miniature optical planar camera based on a wide-angle metasurface doublet corrected for monochromatic aberrations," arXiv:1604.06160, 1-31 (Oct. 2016) 31 pages.
Arbabi, E., et al., "Multiwavelength Polarization Insensitive Lenses Based on Dielectric Metasurfaces with Meta-Molecules." Optica 3, 628-633 (Jun. 2016). 6 Pages.
Arbabi, E., et al., "Dispersionless Optical Dielectric Metasurfaces," CIT-7418-P, 1-2., 2016, 2 pages.
Chen, Y., et al., "Engineering the Phase Front of Light with Phase-Change Material based Planar Lenses," Scientific Reports 5:8660 (2015). 7 pages.
Chong K.E., et al. "Polarization-Independent Silicon Metadevices for Efficient Optical Wavefront Control," Nano let. 15, 5369-5374 (2015).
Decker, M. et al. "High-Efficiency Dielectric Huygens' Surfaces." Advanced Optical Materials 3, 813-820 (2015). 8 Pages.
Donner, J. S., et al., "Fast and Transparent Adaptive Lens Based on Plasmonic Heating." ACS Photonics 2, 355-360 (2015).
Faklis, D., et al., "Spectral Properties of Multiorder Diffractive Lenses." Applied Optics 34(14), 2462-2468 (May 1995). 7 Pages.
Faraon, A., et al., "Flat free-space optical elements based on dielectric metasurfaces," SPIE Newsroom, 2016, 6375.
Gutruf, P. et al., "Mechanically tunabe dieletric resonator metasurfaces at visible frequencies," ACS Nano 10(1), 133-141, (2016).
Huang, Y.-W., et al "Gate-Tunable Conducting Oxide Metasurfaces." Nano Letters 16, 5319-5325, arXiv:1511.09380 preprint (2015). 13 pages.
International Preliminary Report on Patentability for International Application No. PCT/US2017/014197filed on Jan. 19, 2017 on behalf of California Institute of Technology. dated Aug. 2, 2018. 2 pages.
International Search Report for International Application No. PCT/US2017/014197filed on Jan. 19, 2017 on behalf of California Institute of Technology. dated Oct. 31, 2017. 3 pages.
Jahani, S., et al., "All-Dielectric Metamaterials." Nature Nanotechnology 11, 23-36 (Jan. 2016). 14 Pages.
Kamali, S. M., et al., "Decoupling Optical Function and Geometrical Form Using Conformal Flexible Dielectric Metasurfaces." Nature Communications 7:11618 (May 2016). 7 pages.
Kamali, S. M., et al., "Highly Tunable Elastic Dielectric Metasurface Lenses." Laser & Photonics Reviews 10(6), 1002-1008, arXiv:1604.03597 (Oct. 2016). 7 pages.
Koenderink, A F., et al., "Nanophotonics: Shrinking Light-Based Technology." Science 348, 516-521 (May 2015). 6 Pages.
Lalanne, P. "Waveguiding in Blazed-Binary Diffractive Elements." J. Opt. Soc. Am. A 16, 2517-2520 (Oct. 1999). 5 pages.
Lalanne, P., et al., "Blazed Binary Subwavelength Gratings with Efficiencies Larger than those of Conventional Echelette Gratings." Optics Letters 23, 1081-1083 (Jul. 1998). 4 pages.
Lee, J. et al., "Giant Nonlinear Response from Plasmonic Metasurfaces Coupled to Intersubband Transitions." Nature 511, 65-69 (Jul. 2014). 11 pages.
Li, X., et al., "Tunable Binary Fresnel Lens Based on Stretchable PDMS/ CNT Composite," in "Solid-State Sensors, Actuators and Microsystems (TRANDUCERS), 2015 Transducers—2015 18th International Conference on IEEE," 2041-2044 (2015).
Ni X., et al., "Ultra-Thin, Planar, Babinet-Inverted Plasmonic Metalenses." Light: Science & Applications 2, e72 (2013). 6 pages.
Non-Final Office Action for U.S. Appl. No. 15/948,677, filed Apr. 9, 2018 on behalf of California Institute of Technology. dated Jul. 9, 2019. 16 pages.
Notice of Allowance for U.S. Appl. No. 15/948,677, filed Apr. 9, 2018 on behalf of California Institute of Technology. dated Sep. 25, 2019. 11 pages.
Pelrine, R., et al., "High-Speed Electrically Actuated Elastomers with Strain Greater Than 100%," Science 287, 836-839 (2000).
Rogers, J.A., et al., "Materials and Mechanics for Stretchable Electronics," Science 327, 1603-1607 (2010).
Sauvan, C., et al., "Broadband Blazing with Artificial Dielectrics." Optics Letters 29, 1593-1595 (Jul. 2004). 4 pages.
Silva, A., et al., "Performing mathematical operations with metamaterials," Science 343, 160-163 (2014).
Simonov, A.N., et al., "Light Scanner Based on a Viscoelastic Strectchable Grating." Optics Letters 30, 949-951 (2005).
Wang, Q., et al., "Optically Reconfigurable Metasurfaces and Photonic Devices Based on Phase Change Materials." Nature Photonics 10, 60-65 (2016). 13 pages.
Written Opinion for International Application No. PCT/US2017/014197 filed on Jan. 19, 2017 on behalf of California Institute of Technology. dated Oct. 31, 2017. 3 pages.
Yao, Y., et al., "Electrically Tunable Metasurface Perfect Absorbers for ultrathin mid-Infrared optical Modulaters," Nano Letters 14, 6526-6532 (2014).
Yin, X., et al., "Photonic Spin Hall Effect at Metasurfaces." Science 339, 1405-1407 (Mar. 2013). 4 pages.
Yu Y.F., et al., "High-transmission dielectric metasurface with 2n phase control at visible wavelengths," Laser Photon. Rev. 9, 412-418 (2015).
Non-Final Office Action for U.S. Appl. No. 15/410,735, filed Jan. 19, 2017 on behalf of California Institute of Technology. dated Dec. 19, 2019. 20 Pages.

\* cited by examiner

PLANAR DIFFRACTIVE DEVICE WITH MATCHING DIFFRACTION SPECTRUM

CROSS REFERENCE TO RELATED APPLICATIONS

The present application claims priority to U.S. Provisional Patent Application No. 62/208,447, filed on Aug. 21, 2015, and may be related to U.S. patent application Ser. No. 15/096,615, "MULTI-WAVELENGTH OPTICAL DIELECTRIC METASURFACES", filed on Apr. 12, 2016, the disclosures of both of which are incorporated herein by reference in their entirety.

STATEMENT OF INTEREST

This invention was made with government support under Grant No. W911NF-14-1-0345 awarded by the Army Research Office. The government has certain rights in the invention.

TECHNICAL FIELD

The present disclosure relates to diffraction devices. More particularly, it relates to a planar diffractive device with matching diffraction spectrum.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
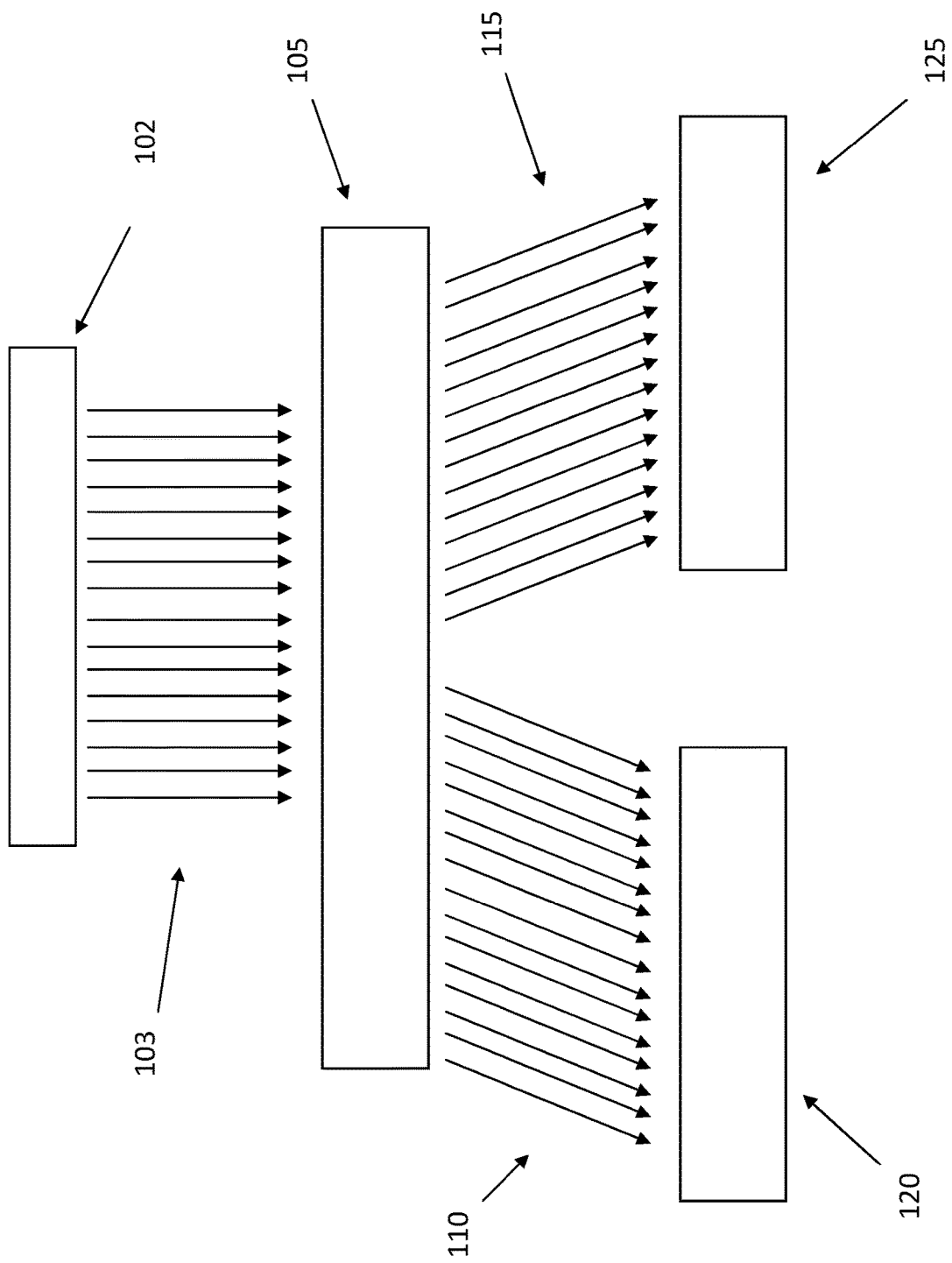
FIG. 1 illustrates an exemplary embodiment of a detecting device.

In a first aspect of the disclosure, a structure is described, the structure comprising: a diffractive optical element configured to diffract a first Raman signal from a target molecule to a first location and a second Raman signal from a reference molecule to a second location, wherein the first location is different from the second location; a first photodetector at the first location; and a second photodetector at the second location.

In a second aspect of the disclosure, a method is described, the method comprising: choosing a target molecule; choosing a reference molecule; and fabricating a diffractive optical element configured to diffract a first Raman signal from a target molecule to a first location and a second Raman signal from a reference molecule to a second location, wherein the first location is different from the second location.

DETAILED DESCRIPTION

Optical spectroscopy is an analytical technique widely used in determining the chemical composition of various compounds. Raman spectroscopy, in particular, is a very powerful technique to detect minute amounts of specific molecules dispersed in a solution or on a surface. Due to its high specificity, Raman spectroscopy can be employed as a non-invasive technique to detect the concentration of various chemical compounds in the human body, for example glucose. In some embodiments, a glucose sensor can be attached to a portable electronic device, like a smart watch.

In Raman sensing of glucose, a laser illuminates through the skin into the tissue and excites a Raman-scattered signal. This signal is collected and read out using a spectrometer. The concentration of glucose can be determined from the strength of the Raman signal. The strength of the signal can be either absolute, or relative to a different molecule.

There are a few challenges in building a portable Raman sensor for glucose. The Raman signal can be very weak and hard to detect, and thus a very sensitive detection method is advantageous. A highly compact and efficient dispersive device is also advantageous, in order to be incorporated in a portable device.

In the present disclosure, a planar diffractive optical device is described that is specifically designed to filter and diffract in a deterministic way, the spectrum associated with one or more chemical compounds of interest. The diffracted spectrum can then be read out using a photo detector, and the concentration of the molecule can then be determined. In other words, the sensing device is tuned to the specific spectrum that is to be detected, in order to maximize detection of the signal of interest relative to detection of other signals. For example, the device may be tuned to detect the signal from glucose detection instead of indiscriminately detect any signal regardless of the specific molecule being detected. By being tuned to a specific molecule, the device can detect weaker signals as it inherently detects the desired molecule better than other molecules. The device is based on one or more layers, or dielectric meta-surfaces, stacked on top of each other. The exact design of the meta-surfaces can be determined via methods such as convex optimization, adjoint state optimization, or genetic algorithms.

FIG. 1 illustrates an exemplary embodiment of the devices of the present disclosure. The diffractive optical element (105) is built such that the Raman peaks of glucose are filtered and diffracted (110) towards one photodetector (120), while the Raman peaks of another molecule (e.g. hemoglobin) used as a reference (named reference molecule) are filtered and diffracted (115) towards another photodetector (125). The relative difference in the signal incident on the two detectors (120,125) can be monitored over time. If a reference molecule with constant concentration is chosen, then the relative signal detected on the two detectors (120,125) will give information about the concentration of glucose in the target solution.

The device of FIG. 1 can be considered a metasurface filter designed specifically to filter and diffract spectral peaks associated with a specific molecule (glucose Raman lines for example). The spectral lines associated with the target molecule (glucose) are incident on one photodetector, while the spectral lines associated with a reference molecule (hemoglobin for example) are incident on another photodetector. The relative difference in signal on the two photodetectors can be used to determine the absolute concentration of the target molecule. A similar setup could be used to detect other molecules instead of glucose, and different molecules could be used as the reference molecule.

One advantage of the technique described herein is that the entire Raman spectrum of the target molecule, e.g. glucose, is sent to one photodetector thus improving the signal to noise ratio. The relative monitoring of the Raman signal of the target molecule (e.g. glucose) compared to another reference molecule is advantageous because the glucose concentration can be monitored even if the absolute Raman signal varies significantly over time.

In some embodiments, the filter that separates the Raman signal of the target and reference molecules can be composed of several stacked metasurfaces designed to filter and disperse the wavelengths associated with the Raman spectrum of specific molecules (glucose for example). Optical metasurfaces are optical components where the amplitude and phase of the transmitted light at different wavelengths is controlled by design. The filter can be designed using techniques such as convex optimization, adjoint state optimization, or genetic algorithm, as it has been done for on-chip photonic devices.

As visible in FIG. 1, a light source may be used to illuminate a sample (102), for example a container holding a solution with the target molecules and reference molecules, with the resulting Raman signal (103) incident on a diffractive optical element (105).

Figure 2:
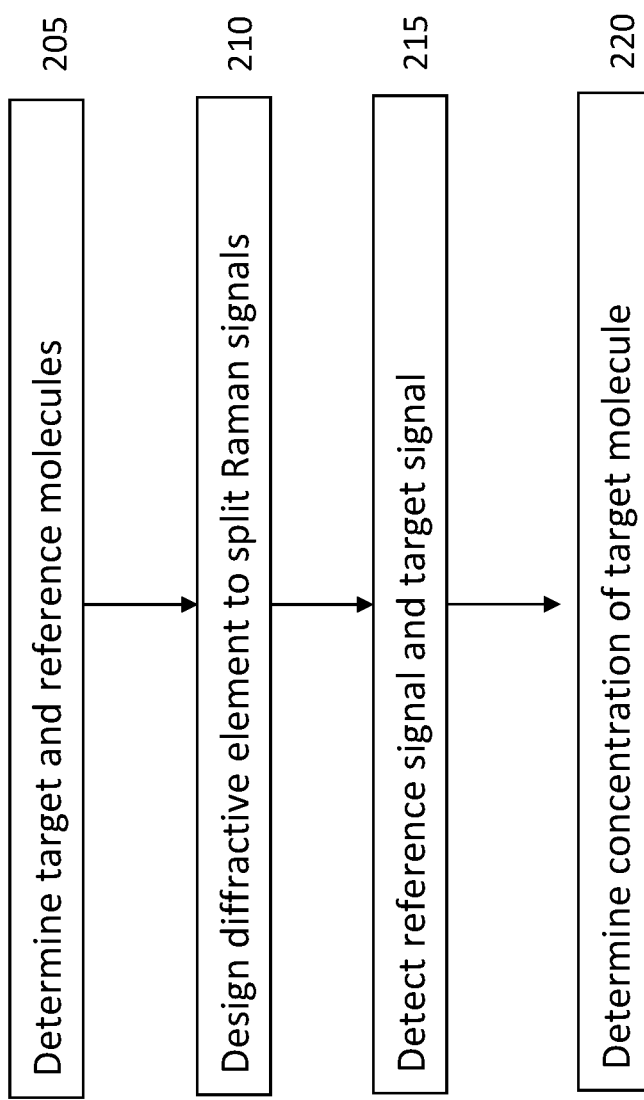
FIG. 2 illustrates an exemplary flowchart of a method to detect molecules.

The method of the present disclosure can be summarized in the flowchart of FIG. 2: determine a target and reference molecule, for example glucose and hemogoblin (205); design the diffractive element to split the Raman signals of the reference and target molecules (210); detect the reference and target signals (215); determine the concentration of target molecules (220) based on the reference and target signals.

In some embodiments, the ratio of the concentrations for the target and reference molecules is determined from the ratio of the intensities detected on the photodetectors. The concentration of the reference molecule is known in advance in order to determine the concentration of the target molecule. The concentration of the target molecule can be determined from a calibration table compiled in advance using solutions with known concentrations.

In some embodiments, if the concentration of the reference molecule and the intensities at the two photodetectors are known, the fourth, unknown quantity, that is the concentration of the target molecule, can be immediately calculated if the signal at the photodetector has a linear dependence on the concentration. In other embodiments, the dependence is not linear, and therefore a lookup table can be used, with photodetector values calibrated with solutions having known concentrations. For example, the reference table contains information to determine the concentration of the target molecule knowing the concentration of the reference molecule and the ratio of the two detector intensities.

In some embodiments, the metasurfaces are composed of silicon nano-posts. For example, the metasurfaces comprise a substrate layer and an array of silicon nano-posts whose size and arrangement are determined based on the desired operational wavelength. Examples of metasurfaces can be found, for example, in Ref. [3]. Metasurfaces are planar structures that modify the polarization, phase and amplitude of transmitted or reflected light. For example, silicon posts of helliptical cross section, arranged in an hexagonal lattice with different orientation can be used. In other embodiments, other types of metasurfaces composed of nano-scale structures could be used.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

[1] Shao, J. W., M. M. Lin, Y. Q. Li, X. Li, J. X. Liu, J. P. Liang, and H. L. Yao, In Vivo Blood Glucose Quantification Using Raman Spectroscopy, Plos One, 2012. 7(10).

[2] Piggott, A. Y., J. Lu, K. G. Lagoudakis, J. Petykiewicz, T. M. Babinec, and J. Vuckovic, Inverse design and demonstration of a compact and broadband on-chip wavelength demultiplexer, Nature Photonics, 2015. 9(6): p. 374.

[3] Arbabi A., Horie Y., Bagheri M., Faraon A., Dieletric metasurfaces for complete control of phase and polarization with subwavelength spatial resolution and high transmission, Nature Nanotechnology—Letters, August 2015.

What is claimed is:

1. A method comprising:
    providing a sample containing target molecules and reference molecules, wherein the reference molecules are of a predetermined concentration in the sample;
    generating a Raman signal from the sample by illuminating the sample;
    providing a dielectric optical metasurface configured to diffract a Raman signal generated from said sample into a first Raman signal and a second Raman signal, the first Raman signal essentially consisting of first Raman peaks from the target molecules to a first location and a second Raman signal essentially consisting of second Raman peaks from the reference molecules to a second location, wherein the first location is different from the second location and both the first location and the second locations are on a same side of the dielectric optical metasurface opposite to a side facing the target and reference molecules; and
    diffracting said Raman signal from the sample into said dielectric optical metasurface into the first Raman signal and the second Raman signal by directing the Raman signal from the sample into the dielectric optical metasurface.

2. The method of claim 1, wherein the target molecule is glucose.

3. The method of claim 2, wherein the reference molecule is hemoglobin.

4. The method of claim 1, further comprising measuring a relative difference of the first Raman signal and the second Raman signal over time and determining an absolute concentration of the target molecule based on the measuring.

* * * * *